United States Patent [19]

Shimizu et al.

[11] Patent Number: 4,515,785

[45] Date of Patent: May 7, 1985

[54] NEEM BARK EXTRACTS

[75] Inventors: Masaki Shimizu, Tokyo; Tadashi Sudo, Honmachi; Takeo Nomura, Hino, all of Japan

[73] Assignee: Terumo Corporation, Tokyo, Japan

[21] Appl. No.: 531,591

[22] Filed: Sep. 13, 1983

Related U.S. Application Data

[63] Continuation of Ser. No. 290,877, Aug. 7, 1981, abandoned.

[30] Foreign Application Priority Data

Aug. 19, 1980 [JP] Japan .............................. 55-113784
Sep. 8, 1980 [JP] Japan .............................. 55-124351
Sep. 24, 1980 [JP] Japan .............................. 55-131669

[51] Int. Cl.³ ............................................ A61K 35/78
[52] U.S. Cl. .................................................. 424/195.1
[58] Field of Search ........................................ 424/195

[56] References Cited

FOREIGN PATENT DOCUMENTS 10124 4/1978 Japan .................................. 424/195
13689 5/1978 Japan .................................. 424/195

OTHER PUBLICATIONS

Tetrahedron 1960, vol. 10, pp. 45–54, Pergamon Press Ltd. Ireland.
Cancer Research, vol., 27, Feb. 1967 Number 2, pp. 6–8, 11 and 105.

*Primary Examiner*—Albert T. Meyers
*Assistant Examiner*—John W. Rollins
*Attorney, Agent, or Firm*—Frishauf, Holtz, Goodman & Woodward

[57] ABSTRACT

Neem bark extracts produced by pre-treating the bark of neem with an organic solvent having a dielectric constant of 10 or lower, for example, benzene or ethyl acetate and subjecting the residue obtained by the pre-treatment to extraction with a hydrophilic organic solvent having a dielectric constant from 15 to 35, for example, methanol or ethanol and recovering the neem bark extracts from the hydrophilic organic extraction solvent.

9 Claims, 3 Drawing Figures

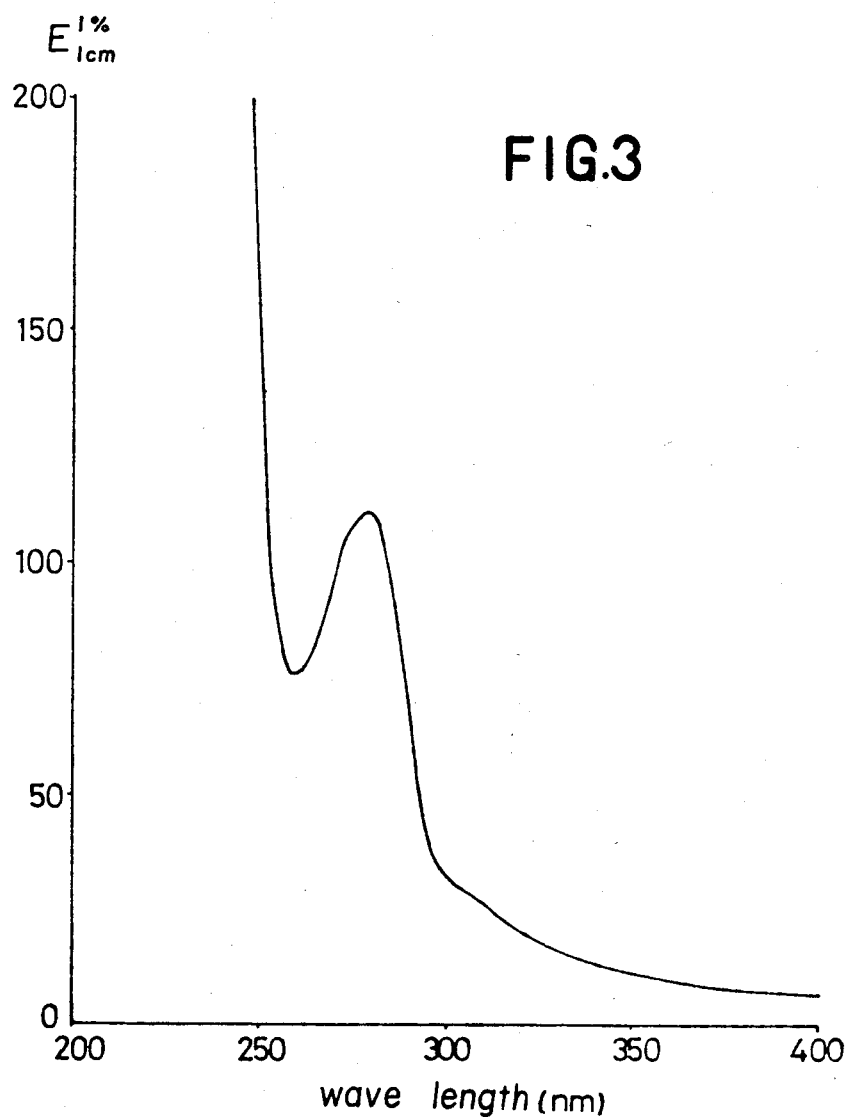

NEEM BARK EXTRACTS

This application is a continuation of application Ser. No. 290,877, filed Aug. 7, 1981, now abandoned.

BACKGROUND OF THE INVENTION

1. Field of the Invention

This invention relates to novel neem bark extracts. The neem bark extracts according to the invention possess antimitotic activity in sea urchin eggs and activity against mouse L-5178Y cells and transplanted sarcoma 180 tumors.

As a result of extensive studies on pharmacological actions of constituents contained in the neem materials, it has now been found that consecutive treatments of the neem bark with two solvents of different dielectric constants result in the constituents possessing the antineoplastic activity mentioned above.

It is therefore the object of the present invention to provide neem bark extracts which are active against mouse L-5178Y cells and transplanted sarcoma 180 tumors.

2. Description of the Prior Art

It is heretofore known that neem extracts contain various pharmacologically active constituents. In fact, there are disclosed a method of producing cosmetics for the skin from the bark, leaves, flowers, fruits, branch, root epidermis or resin of neem by extracting the same with water or a hydrophilic solvent or by finely pulverizing the same (Japanese Patent Publication Nos. 28853/77, 28854/77 and 10125/78); a method of preparing from such neem materials the constituents possessing gastrointestinal and hepatic function-improving activities by extracting the same with a hydrophilic solvent and/or hot water (Japanese Patent Publication No. 10124/78); and a method of preparing from such neem materials the constituents that are effective for the therapy of dermatological and rheumatic diseases by extracting the same with a hydrophobic solvent (Japanese Patent Publication No. 13689/78). These methods are distinct from the present invention in that there are involved in order to produce the active constituents no pretreatment but direct extraction process only.

SUMMARY OF THE INVENTION

The present invention relates to neem bark extracts which are obtained by subjecting the neem bark to an extraction process with an organic solvent having a dielectric constant of 10 or lower and subsequently subjecting the residue from the first extraction to extraction with a hydrophilic organic solvent having a dielectric constant from 15 to 35. As described below, the neem extracts according to the invention exhibit antimitotic activities in fertilized eggs of sea urchin as well as growth-inhibitory actions against mouse sarcoma 180 ascites and solid tumors and mouse L-5178Y cells.

Neem is a large tree 10 m. or higher in height which is native in the tropics and called *Melia azadirachta* as a botanical name. Its bark is utilized in the present invention. The bark is preferably dried and finely divided for use in the invention.

According to the present invention, an extraction process in which the neem bark is treated with an organic solvent having a dielectric constant of 10 or lower is employed as a pretreatment for extracting the active constituents. Illustrative of such solvent are benzene, toluene, xylenes, n-hexane, chloroform, carbon tetrachloride, ethyl acetate and the like. The treatment prior to the extraction is carried our for a period of several hours to overnight. The residue from the first extraction is extracted with a hydrophilic organic solvent. As examples of the solvent used in this step are mentioned lower alcohols such as methanol, ethanol, propanols and n-butanol, pyridine, acetone and the like. The extraction is carried out for several hours to overnight in a conventional manner. Removal of the solvent from the extract, for example, by distillation affords the neem bark extract according to the present invention. Alternatively, the extract may be purified to a neem bark extract of a higher purity using the process that follows. The neem bark extract obtained as set forth above is dissolved in an aqueous lower alcohol such as aqueous methanol or ethanol, contacting the resulting solution with a non-polar porous polymer resin having a macroreticular structure for adsorption chromatography such as, for example, Amberlite ® XAD-2, XAD-4 (Rhom and Haas), Bio Beads TM SM-1, SM-2 (Biorad), Diaion ® HP-10, HP-20, HP-30 (Mitsubishi Chemical Industries) or the like. Bio-Beads SM-1 and SM-2 are non-polar neutral, porous styrene-divinyl benzene copolymer beads. Diaion HP-10, HP-20 and HP-30 are styrene-divinyl benzene copolymers in bead form. The adsorption resin is treated with 10% aqueous methanol, followed by elution of the adsorbed materials with 50% aqueous methanol. Removal of the solvent from the eluate, for example, by distillation yields the desired neem bark extract.

The neem bark extracts of the present invention have the following characteristics:

(1) Appearance
  Brown powders
(2) IR absorption spectrum
  As shown in FIGS. 1 and 2.
  IR $\nu_{max}^{KBr}$ cm.$^{-1}$: 3400, 1600, 1435.
(3) UV absorption spectrum
  As shown in FIG. 3 methanol was employed as the solvent.
  UV λmas. : 279 nm. λmin. : 259 nm.
(4) Solubility
  ca. 40 mg./ml. in water, 50 mg./ml. in methanol, ca. 20 mg./ml. in ethanol, ca. 1.5 mg./ml. in acetone and sparingly insoluble in benzene, chloroform, ethyl acetate or n-hexane.
(5) Treatment at varying pHs
  The present extract does not lose its activities when treated at 60° C. for 30 min. in an aqueous solution at a pH of 2, 7 or 9.

The neem bark extracts of the present invention have activity against mouse L-5178Y cells and transplanted sarcoma 180 tumors. They may be administered parenterally, for example, by subcutaneous, intravenous or intramuscular injection, or orally in the form of tablets, capsules, granules, powders, syrup or the like. Dose level of the present extracts is from ca. 1 to 5 g. per day for male adults though it may be varied depending upon age, bodyweight and conditions of the patient administered.

The extracts of the present invention are formulated in conventional manners. For example, dried powders of the present extract are placed in a vessel such as a vial. Separately, a physiological saline solution, aqueous glucose solution or suspension of carboxymethylcellulose (CMC) is prepared in a vessel such as an ampule. The powders are dissolved or suspended when used.

Alternatively, an emulsion containing the extract may be injected. In the case of a water-in-oil (w/o) emulsion, for example, a combination of a mineral oil such as liquid paraffin or a vegetable oil such as sesame oil or peanut oil with a surfactant such as sorbitan aliphatic esters is employed.

BRIEF DESCRIPTION OF THE DRAWINGS

FIG. 3 is an UV absorption spectrum of the same extract as in FIG. 2.

DESCRIPTION OF THE PREFERRED EMBODIMENTS

The invention will be described in more detail in conjunction with the following examples, test examples and formulation examples.

Example 1

Figure 1:
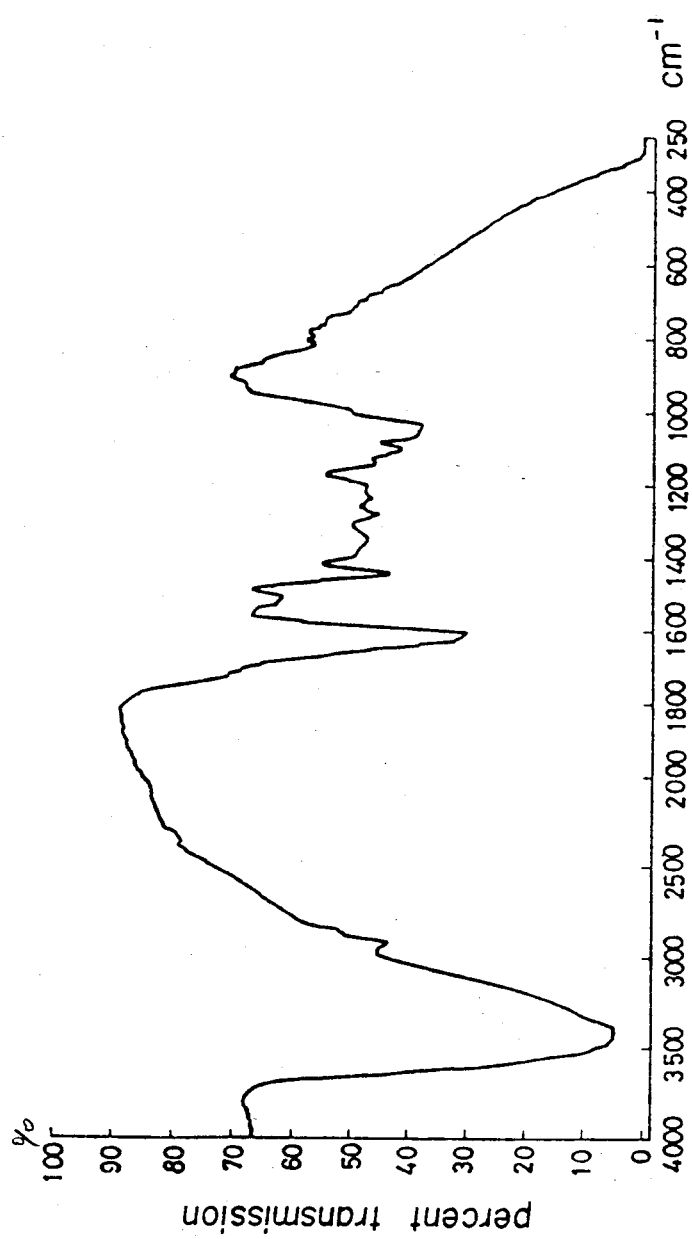
FIG. 1 is an IR absorption spectrum of the neem bark extract obtained in Example 1.
Figure 2:
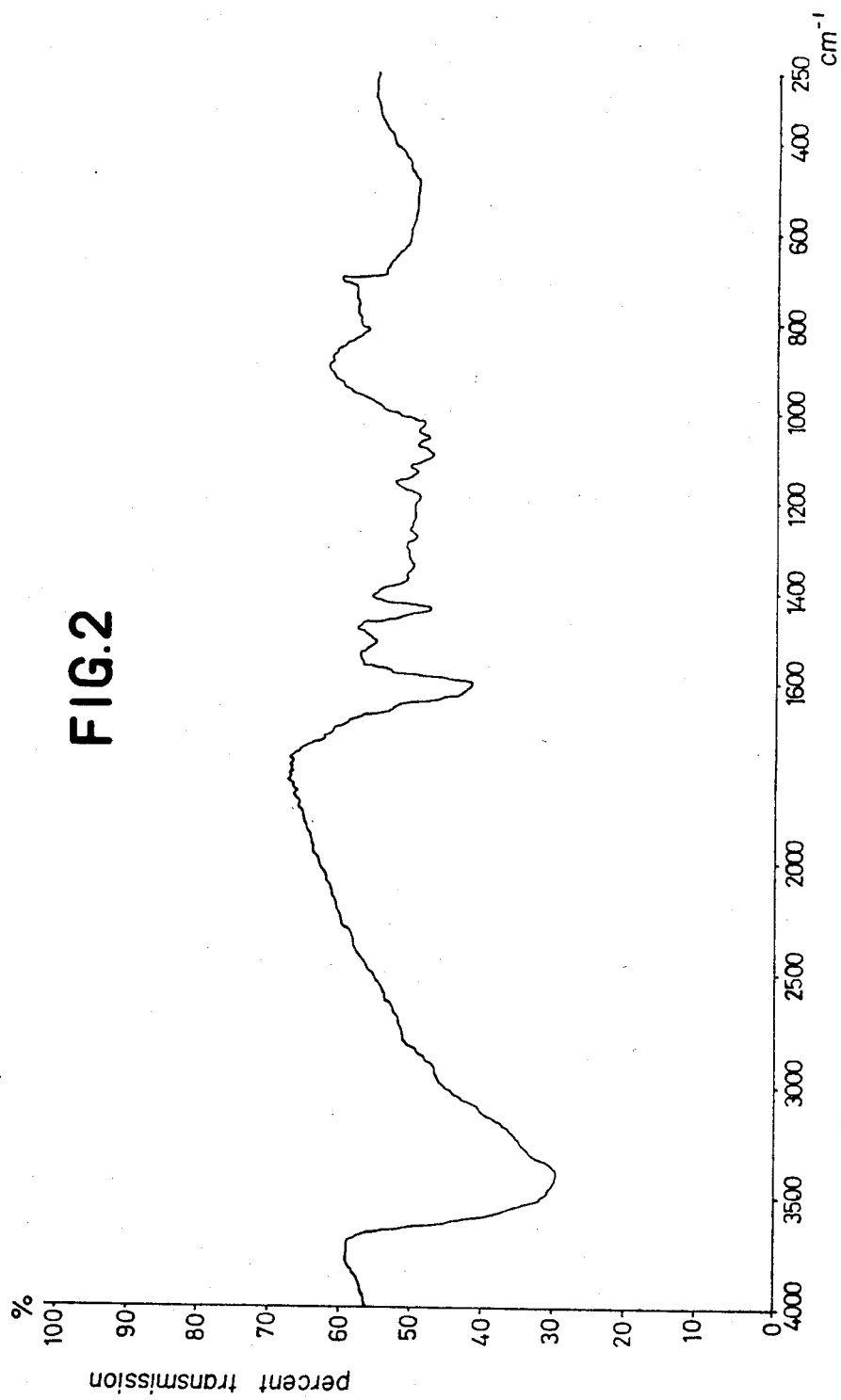
FIG. 2 is an IR absorption spectrum of the neem bark extract obtained in Example 5.

To 10 g. of the dry neem bark was added 100 ml. of benzene. The mixture was allowed to stand for 1 hour with shaking at intervals to expedite extraction. The resulting mixture was filtered, and to the residue was added 100 ml. of benzene. The mixture was treated in the same way as above. The benzene extraction was repeated three times in total. The combined benzene extracts were concentrated to dryness to give powders. The powders thus obtained are designated the benzene fraction. To the residue from the benzene extractions was added 100 ml. of methanol, and the mixture was subjected to the same procedures as described with benzene. The powders then obtained are designated the methanol fraction. An IR absorption spectrum of the methanol fraction is shown in FIG. 1.

The obtained dry powders weighed 48.2 mg. for the benzene fraction and 385.4 mg for the methanol fraction.

Example 2

The same extraction process as in Example 1 was applied to 10 g. of the dry neem leaves. There were produced 120.2 mg. of a benzene fraction and 682.5 mg. of a methanol fraction respectively in dry powders.

Example 3

The same procedures as in Example 1 were repeated with 10 g. of the dry neem bark except that ethyl acetate was employed in place of the benzene. There were obtained 86.0 mg. of an ethyl acetate fraction and 360.3 mg. of a methanol fraction respectively in dry powders.

Example 4

The same procedures as in Example 1 were repeated with 10 mg. of the dry neem bark except that ethanol was employed in place of the methanol. There were obtained 43.9 mg. of a benzene fraction and 334.8 mg. of an ethanol fraction respectively in dry powders.

The neem extracts produced as described above were tested using sea urchin eggs, mouse L-5178Y cells, and mouse sarcoma 180 ascites and solid tumors. Activities, effective dose levels and effects in comparison with known antitumor agents were examined. Results of the tests are described below.

Test I

Antimitotic activities of the neem extracts of the present invention were determined using sea urchin eggs as follows.

Fertilized eggs of sea urchin, *Hemicentrotus pulcherrimus* or *Anthocidaris crassispina* numbered 200–300 together with 2 ml. of sea water were placed in a test tube. Immediately thereafter, 0.2 ml. of an aqueous or DMSO (dimethyl sulfoxide) solution of the test materials as obtained in the above examples was added to the test tube. Cell division of the fertilized eggs was then observed microscopically. Results are shown in Table I below. In the table, +++, ++, * and - represent complete inhibition of the egg division, about 50–80% inhibition of the egg division, one or two divisions of the eggs allowed and no inhibition of the egg division, respectively.

TABLE I

Effect on the cell division of sea urchin zygotes

| Portion of neem | Fraction (Example No.) | Concentration of the test solution (mg/ml) | | |
|---|---|---|---|---|
| | | 0.25 | 0.50 | 1.0 |
| Bark | Benzene (1) | - | - | - |
| | Methanol (1) | - | ++ | +++ |
| | Ethyl acetate (3) | - | - | * |
| | Methanol (3) | - | ++ | +++ |
| | Benzene (4) | - | - | * |
| | Ethanol (4) | - | * | ++ |
| Leaves | Benzene (2) | - | - | - |
| | Methanol (2) | - | - | * |

It can easily been seen from the results of the above test in Table I that the bark fractions methanol (1) methanol (2) and ethanol (4) and the leaf fraction methanol (2) effectively inhibit cell division of fertilized sea urchin eggs as compared with the other fractions.

More particularly, the methanol (1) and methanol (2) fractions inhibit the cell division of the eggs completely in a concentration of the test solution of 1 mg./ml. 50–80% inhibition is observed with the ethanol (4) fraction, and only up to one or two cell divisions are allowed with the methanol fraction (2) of the leaves. The benzene (1) fraction in the table above corresponds to the pharmacologically active ingredient of neem as disclosed in Japanese Patent Publication No. 13689/78. It is therefore evident that the neem extracts according to the present invention are far more pharmacologically active than the former.

Test II

The following test was run for the methanol (1) fraction which exhibited a high antimitotic activity in fertilized eggs of sea urchin in Test I.

A test solution was added to sea urchin eggs, followed by addition of the sperm cells. Then, observation was made as to whether fertilization was inhibited. 100% and 80% inhibitions of the fertilization of sea urchin eggs were observed with the test solution at concentrations of 0.8 mg./ml. and 0.16 mg./ml., respectively. The test solution at a concentration of 0.032 mg./ml. did not inhibit the fertilization, but division of the eggs was suspended following one division.

When the test solution at a concentration of 0.8 mg./ml. was added 15 min. after fertilization of the eggs, the division was suspended following two divisions.

Results of the tests as described above revealed that the neem extracts according to the invention inhibited not only the cell division but also fertilization of the eggs. Those pharmacologically active ingredients which inhibit the fertilization and division of eggs can find a wide range of applications as agrochemicals and pharmaceuticals. Effective dose level, formulation and toxicity consideration may be determined in accordance with the intended area of use.

Text III (Effects on mouse L-5178Y cells)

(1) Preparation of the cell culture medium

A medium containing $1 \times 10^5$ cells/ml. was prepared using mouse L-5178Y cells cultivated on RPMI-1640 medium containing 10% fetal bovine serum for 3 days. The medium was placed in a 96-well U-type microplate in an amount of 50 µl. per well.

(2) Method of evaluation

A portion of the test material, which was one of the extracts according to the invention described in the above examples, was dissolved in the medium to a final concentration in the medium as shown in Table II below. The amount of the solution per well was 60 µl. The test material thus prepared was incubated in a carbon-dioxide incubator at 37° C. for 2 days. After completion of the incubation, the cells were collected and counted well by well, and the cell counts were compared with cell count of the control which contained no test material. The cell could of the control was approximately $8.6 \times 10^5$/ml. For activity comparison's sake, the same test was done with mitomycin C (MMC) or bleomycin (BLM). In the table below, T/C represents the ratio of count of the cells treated with the test material to that with no test material added. $ID_{50}$ is the concentration of the test material required for decreasing concentration of the cells to ½ that of the control.

TABLE II

Effects on mouse L-5178Y cells

| Portion of neem | Example (Example No.) | Concentration of test material (µg./ml.) | T/C (%) | $ID_{50}$ (µg./ml.) |
|---|---|---|---|---|
| Bark | Benzene (1) | 100 | 98.1 | — |
| | | 30 | 105 | |
| | | 15 | 114 | |
| | Ethyl acetate (3) | 100 | 94.5 | — |
| | | 30 | 99.8 | |
| | | 15 | 100.0 | |
| | Methanol (1) | 100 | 1.0 | 21 |
| | | 30 | 15.0 | |
| | | 20 | 60.0 | |
| | Ethanol (4) | 100 | 17.5 | 38 |
| | | 31 | 58.0 | |
| | | 15 | 83.0 | |
| Leaves | Benzene (2) | 100 | 102.4 | — |
| | | 31 | 110.3 | |
| | | 15 | 108.4 | |
| | Methanol (2) | 100 | 94.8 | — |
| | | 31 | 99.2 | |
| | | 15 | 115 | |
| Control | MMC | 1.0 | 13.4 | 0.09 |
| | | 0.3 | 24.7 | |
| | | 0.1 | 47.9 | |
| | BLM | 100 | 8.8 | 7.8 |
| | | 10 | 46.1 | |
| | | 5 | 57.1 | |

(3) Results

The results with various fractions as produced in the above examples and comparison agents were shown in Table II. The benzene and ethyl acetate fractions of the neem bark and the methanol fraction of the leaves respectively exhibited slight activities. It is evaluated that the activities are very weak with the $ID_{50}$ values being very high. On the other hand, the methanol or ethanol fraction were highly active. Although the activities are below the activities of MMC and BLM, they may be considered to be high enough when the active ingredient contained in the methanol or ethanol fraction is taken into consideration.

Test IV (Effects on sarcoma 180 ascites tumor)

(1) Preparation of the test material

A portion of each of the extraction fractions was suspended or dissolved in 0.5% suspension of carboxymethylcellulose (CMC) in a phosphate buffered saline solution (PBS commercially available from GIBCO Laboratories, containing ca. 9.5 mM phosphate) to a predetermined concentration.

(2) Transplantation of sarcoma 180 tumor cells

Mouse sarcoma 180 tumor cells which have been subcultivated intraperitoneally in ICR mice were drawn from the mouse together with the ascites and diluted with physiological saline solution to a cell count of $10^8$ per ml. The tumor cell suspension thus prepared was transplanted by means of a syringe intraperitoneally into 4 week-old male ICR mice at a dose of 0.1 ml. Consequently, the cell count transplanted per mouse was $1 \times 10^7$.

(3) Administration of the test material

The test material as prepared above was intraperitoneally administered at a dose of 0.1 ml. per mouse for 4 days once a day from the next day of the transplantation of mouse sarcoma 180 tumor cells. A group of 6 mice was employed for each concentration of each test material. As active controls were used MMC, BLM, actinomycin D (ACD), 5-fluorouracil (5-Fu) and cyclophosphamide (CYP). As a control was administered the CMC-containing PBS as described above only in the same way as above. The dose is expressed as weight per kg. bodyweight of mouse.

(4) Method of evaluation

On the 7th day of transplantation of the tumor cells the bodyweight of each mouse was measured (X). Then, ascites was thoroughly drawn from the mouse, followed by measurement of the bodyweight (Y). X-Y is taken as the amount of ascites.

The drawn ascites was the introduced into a hematocrit tube and then centrifuged at 15,000 G for 5 minutes using a hematocrit rotor at a low temperature. There was thus made determination of the ascitocrit value, that is, proportion of the cells present in the ascites which corresponded to the hematocrit value in hematology. The value multiplied by volume of the ascites gives the volume of the cells present in the ascites. This is designated as total packed cell volume (TPCV). In case of the control, the total volume of ascites was 6-10 ml., and the TPCV was 1.6-2.5 ml.

Effect on the tumor was rated ineffective (−) when the TPCV ratio of the treated to the control (T/C) was 100-66%, plus 1 (+) when it was 65-41%, plus 2 (++) when it was 40-11%, and plus 3 (+++) when it was 10-0%. Test results for the materials according to the present invention in comparison with the prior art materials are shown in Table III below.

TABLE III

Effects on sarcoma 180 ascites tumor

| Portion of neem | Fraction (Example No.) | Dose (mg./kg.) | T/C (%) | Rating |
|---|---|---|---|---|
| Bark | Benzene (1) | 100 | 97.6 | — |

TABLE III-continued

Effects on sarcoma 180 ascites tumor

| Portion of neem | Fraction (Example No.) | Dose (mg./kg.) | T/C (%) | Rating |
|---|---|---|---|---|
| | Benzene (4) | 100 | 95.2 | — |
| | Ethyl acetate (3) | 100 | 96.8 | — |
| | Methanol (1) | 20 | 94.8 | — |
| | | | 84.8 | — |
| | | 50 | 34.3 | ++ |
| | | | 32.2 | ++ |
| | | 100 | 4.8 | +++ |
| | | | 10.8 | ++ |
| | | | 12.4 | ++ |
| | Methanol (3) | 100 | 8.5 | +++ |
| | Ethanol (4) | 100 | 14.8 | ++ |
| | | | 18.5 | ++ |
| Leaves | Benzene (2) | 100 | 94.8 | — |
| | Methanol (2) | 100 | 76.8 | — |
| Control | MMC | 0.5 | 0 | +++ |
| | | 1.5 | 0 | +++ |
| | BLM | 10 | 0 | +++ |
| | ACD | 0.1 | 0 | +++ |
| | 5-Fu | 20 | 0 | +++ |
| | CYP | 33 | 0 | +++ |
| | | 67 | 0 | +++ |

(5) Results

No effects at all were observed with the benzene and ethyl acetate fractions of the neem bark as well as all of the neem leaf fractions. On the other hand, there were observed high activities especially with the methanol and ethanol fractions of neem bark. Although the activities were below the activities of the active controls, MMC, BLM, etc., they may be considered high enough when the active ingredient is contained in such fraction. Further purification of these fractions to give purer active ingredient would result in increased activities. The minimum effective dose for the methanol fraction (1) has been found from dose-T/C relationship in the above table to be approximately 30 mg./kg.

Test V (Effects on sarcoma 180 solid tumor)

(1) Preparation of the test material

Test materials were prepared in the same manner as in Test IV under (1).

(2) Transplantation of sarcoma 180 solid tumor cells

A cell suspension containing $1 \times 10^8$ cells per ml. was prepared in the same way as in Test IV under (2). Four week old-ICR mice was innoculated subcutaneously on the back with 0.1 ml. of the suspenstion by means of a syringe.

(3) Administration of the test material

As in Test IV under (3), a group of 6 animals was used for each concentration of each test material.

(4) Method of evaluation

Grown tumor tissue was resected on the 15th–21st day of the tumor cell transplantation and weighed. An average for the group of 6 animals was taken for the evaluation. The effect was evaluated on the basis of ratio of the average weight for the treated animals to that of the control animals. The average weight was 1.5–3.5 g. for the control animals. Ratios (T/C) of 100–71% were rated ineffective (—), of 70–51% plus 1 (+), of 50–21% plus 2 (++), and of 20–0% plus 3 (+++). Results with the test materials according to the present invention and the prior art agents are shown in Table IV below.

TABLE IV

Effects on sarcoma 180 solid tumor

| Portion of neem | Fraction (Example No.) | Dose (mg./kg.) | T/C (%) | Rating |
|---|---|---|---|---|
| Bark | Benzene (1) | 100 | 86.4 | — |
| | | | 92.0 | — |
| | Benzene (4) | 100 | 91.3 | — |
| | Ethyl acetate (3) | 100 | 94.2 | — |
| | Methanol (1) | 20 | 105.4 | — |
| | | | 128.2 | — |
| | | 50 | 83.9 | — |
| | | | 88.0 | — |
| | | 100 | 40.7 | ++ |
| | | | 65.0 | + |
| | | 200 | 24.1 | ++ |
| | Methanol (3) | 100 | 50.8 | + |
| | Ethanol (4) | 100 | 68.2 | + |
| | | | 51.3 | + |
| Leaves | Benzene (2) | 100 | 93.8 | — |
| | Methanol (2) | 100 | 95.9 | — |
| Control | MMC | 0.5 | 71.0 | — |
| | | 1.5 | 32.5 | ++ |
| | | | 50.2 | + |
| | BLM | 10 | 43.5 | ++ |
| | | | 52.3 | + |
| | ALD | 0.1 | 102.4 | — |
| | 5-Fu | 20 | 47.8 | + |
| | CYP | 33 | 0 | +++ |
| | | 67 | 0 | +++ |

(5) Results

Whereas there were observed no effects at all with the benzene and ethyl acetate fractions of the neem bark as well as all the fractions of the neem leaves, the methanol fractions of the neem bark exhibited high activities. The minimum effective dose for the methanol fraction (1) has been found from dose-T/C relationship to be approximately 65 mg./kg. Although the activities are low as compared with the active controls such as MMC and BLM, further purification of the extracts according to the invention for the active ingredients would lead to higher activities.

Acute Toxicity

The $LD_{50}$ value for the methanol fraction as intraperitoneally administered in ICR male mice weighing 19–21 g. was 1,100 mg./kg. bodyweight.

Example 5

To 100 g. of the dry neem bark was added 1 l. of benzene. The mixture was allowed to stand for 5 hours with shaking at intervals to expedite extraction. The resulting mixture was filtered, and to the residue was added 1 l. of benzene. The mixture was then treated in the same way as above. The benzene extraction was repeated three times in total. To the resulting residue was added 1 liter of methanol. The methanol extraction was repeated three times in total as above. From the combined extracts was removed the solvent on a rotary evaporator to give 3.9 g. of an extract in dry powders. The powdery extract thus obtained, 2.1 g., was dissolved in 1 l. of 10% methanol followed by thorough mixing with 300 ml. of Amberlite XAD-2. The mixture was packed in a column 3.0×40 cm. in size. Through the column were passed 10% aqueous methanol, 50% aqueous methanol and 100% methanol, successively. Each of the eluates was then concentrated to dryness. There were obtained 0.81 g. of the 10% methanol fraction, 0.84 g. of the 50% methanol fraction and 0.22 g. of the 100% methanol fraction, respectively in powders.

Example 6

The same procedures as in Example 5 were repeated except that 1 l. of ethanol was employed in place of 1 l. of methanol used therein as the extract. There were obtained 0.69 g. of the 10% methanol fraction, 0.80 g. of the 50% methanol fraction and 0.33 g. of the 100% methanol fraction, respectively in powdery extract.

Example 7

The same procedures as in Example 5 were repeated except that 1 l. of ethyl acetate was employed in place of 1 l. of benzene used therein for extraction treatment. There were obtained 0.78 g. of the 10% methanol fraction, 0.82 g. of the 50% methanol fraction and 0.24 g. of the 100% methanol fraction, respectively in powdery extract.

The neem extracts produced in Examples 5–7 above were tested for effects on mouse L-5178Y cells, sarcoma 180 ascites and solid tumors according to the methods described in Tests II–IV. Results are shown in Tables V and VI.

TABLE V

Effects on Mouse L-5178Y cells

| Example No. | Methanol fraction | $ID_{50}$ ($\mu g$./ml.) |
|---|---|---|
| Example 5 | 10% MeOH | >100 |
|  | 50% MeOH | 16.5 |
|  | 100% MeOH | 67.5 |
| Example 6 | 50% MeOH | 35.0 |
| Example 7 | 50% MeOH | 18.0 |

TABLE VI

Effects on transplanted sarcoma 180 tumors (mice)

| Type of the tumor | Example No. | Methanol fraction | Dose (mg./kg.) | T/C (%) | Rating |
|---|---|---|---|---|---|
| Ascites tumor | Example 5 | 10% MeOH | 25 | 100.5 | − |
|  |  |  | 50 | 99.2 | − |
|  |  |  | 100 | 98.8 | − |
|  |  | 50% MeOH | 25 | 77.5 | − |
|  |  |  | 50 | 38.0 | ++ |
|  |  |  | 100 | 7.9 | +++ |
|  |  | 100% MeOH | 25 | 102.5 | − |
|  |  |  | 50 | 99.8 | − |
|  |  |  | 100 | 107.3 | − |
|  | Example 6 | 50% MeOH | 50 | 41.3 | + |
|  |  |  | 100 | 10.2 | +++ |
|  | Example 7 | 50% MeOH | 50 | 40.2 | ++ |
|  |  |  | 100 | 8.5 | +++ |
| Solid tumor | Example 5 | 10% MeOH | 25 | 101.3 | − |
|  |  |  | 50 | 89.2 | − |
|  |  |  | 100 | 76.9 | − |
|  |  | 50% MeOH | 25 | 63.6 | + |
|  |  |  | 50 | 60.7 | + |
|  |  |  | 100 | 37.5 | ++ |
|  |  | 100% MeOH | 25 | 99.9 | − |
|  |  |  | 50 | 98.4 | − |
|  |  |  | 100 | 91.7 | − |
|  | Example 6 | 50% MeOH | 50 | 59.0 | + |
|  |  |  | 100 | 45.0 | ++ |
|  | Example 7 | 50% MeOH | 50 | 53.5 | + |
|  |  |  | 100 | 41.2 | ++ |

It is clearly seen from Tables V and VI that the 50% methanol fraction possesses high activity against mouse L-5178Y cells and transplanted sarcoma 180 tumors. The extract has a minimum effective dose of 30 mg./kg. in mice for the ascites tumor and a minimum effective dose of 25 mg./kg. in mice for the solid tumor. Acute toxicity in terms of the $LD_{50}$ in male mice was 390 mg./kg. bodyweight by intraperitoneal administration.

Formulation Example 1

In 500 ml. of sterile 5% glucose solution for injection was suspended 1000 mg. of the neem bark extract produced in Example 1. The suspension was aseptically divided in vials in an amount of 5 ml. per vial and freeze-dried. There was obtained a formulation containing 10 mg. of the neem bark extract per vial. When used, it is suspended in distilled water for injection.

Formulation Example 2

A vial formulation was prepared in the same way as in the above example. There was employed 500 ml. of a 0.5% suspension of CMC J.P. in physiological saline solution for injection in place of 500 ml. of 5% sterile glucose solution for injection. When used, a suspension in distilled water for injection was used.

What we claim is:

1. A neem bark extract which is characterized by being active against mouse L-5178y cells and against transplanted sarcoma 180 tumors produced by contacting the bark of neem which is *Melia azadirachta* with an organic solvent selected from the group consisting of benezene, toluene, xylene, n-hexane, chloroform, carbon tetrachloride and ethylacetate for a time sufficient to form a first liquid extract and a first residue, subjecting said first residue to extraction with a hydrophilic organic solvent selected from the group consisting of methanol, ethanol, propanol, n-butanol, pyridine and acetone for a time sufficient to form a second residue and a second liquid extract comprising solvent and dissolved second extract and removing said solvent from said second extract to form a third residue, dissolving said third residue in a lower alcohol selected from the group consisting of methanol, ethanol, propanol and n-butanol, contacting the resulting solution with a non-polar porous polymer resin having a macroreticular structure in adsorption chromatography whereby said solids of said third residue which are dissolved in said solution are adsorbed on said resin, treating said adsorption resin containing said solids with 10% aqueous methanol followed by elution with from 30 to 50% solutions of methanol and removing the solvent from said eluates to provide said neem bark extract.

2. The neem bark extract of claim 1 wherein the hydrophilic organic solvent is methanol.

3. The neem bark extract of claim 1 wherein the hydrophilic organic solvent is ethanol.

4. The neem bark extract of claim 1 wherein said lower alcohol is methanol.

5. The neem bark extract of claim 1 wherein said lower alcohol is ethanol.

6. The neem bark extract of claim 1 wherein said non-polar porous polymer resin is a copolymer of styrene and divinyl benzene.

7. The neem bark extract of claim 1 wherein the bark of neem is dried and ground prior to contacting said bark with said organic solvent.

8. The neem bark extract of claim 1 wherein the step of contacting said bark with said organic solvent is carried out for between about one hour and twelve hours.

9. The neem bark extract of claim 1 wherein the step of subjecting said first residue to extraction with said hydrophilic solvent is carried out for between about one hour and twelve hours.

* * * * *

UNITED STATES PATENT AND TRADEMARK OFFICE
CERTIFICATE OF CORRECTION

PATENT NO. : 4,515,785

DATED : May 7, 1985

INVENTOR(S) : Masaki SHIMIZU et al.

It is certified that error appears in the above-identified patent and that said Letters Patent is hereby corrected as shown below:

COLUMN 2, line 3, change "our" to --out--.

COLUMN 5, line 29, change "could" to --count--.

COLUMN 7, line 50, change "suspenstion" to --suspension--.

Signed and Sealed this
Ninth Day of December, 1986

Attest:

DONALD J. QUIGG

*Attesting Officer*　　　　*Commissioner of Patents and Trademarks*